(12) United States Patent
Breeuwer

(10) Patent No.: US 7,698,234 B2
(45) Date of Patent: Apr. 13, 2010

(54) CARDIAC PERFUSION ANALYSIS

(75) Inventor: Marcel Breeuwer, Eindhoven (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 1524 days.

(21) Appl. No.: 10/508,451

(22) PCT Filed: Mar. 20, 2003

(86) PCT No.: PCT/IB03/01116

§ 371 (c)(1),
(2), (4) Date: Sep. 21, 2004

(87) PCT Pub. No.: WO03/081508

PCT Pub. Date: Oct. 2, 2003

(65) Prior Publication Data

US 2005/0124861 A1  Jun. 9, 2005

(30) Foreign Application Priority Data

Mar. 25, 2002  (EP) ................... 02076162

(51) Int. Cl.
*G06F 15/18* (2006.01)

(52) U.S. Cl. ............ 706/12; 604/507; 128/898
(58) Field of Classification Search .......... 706/16; 600/509, 443; 700/17, 83
See application file for complete search history.

(56) References Cited

U.S. PATENT DOCUMENTS

| 5,803,910 A | 9/1998 | Ryals | |
|---|---|---|---|
| 2001/0031037 A1* | 10/2001 | Prince et al. | 378/137 |
| 2002/0016548 A1* | 2/2002 | Stadler et al. | 600/509 |

* cited by examiner

*Primary Examiner*—David R Vincent
*Assistant Examiner*—Kalpana Bharadwaj

(57) ABSTRACT

In a method of analyzing a quantity having temporal and spatial variations a multidimensional output data array is formed. The multidimensional output data array comprises array positions arranged along at least a first data-axis and a second data-axis, such as a spatial axis and a temporal axis. Values of the quantity are entered in the multidimensional output data array. Values of the quantity at substantially the same instant are entered at respective positions in the multidimensional output data array at equal positions along the first data-axis. Values of the quantity at substantially the same spatial position are entered at respective positions in the multidimensional output data array at equal positions along the second data-axis.

20 Claims, 2 Drawing Sheets

CARDIAC PERFUSION ANALYSIS

Figure 1:
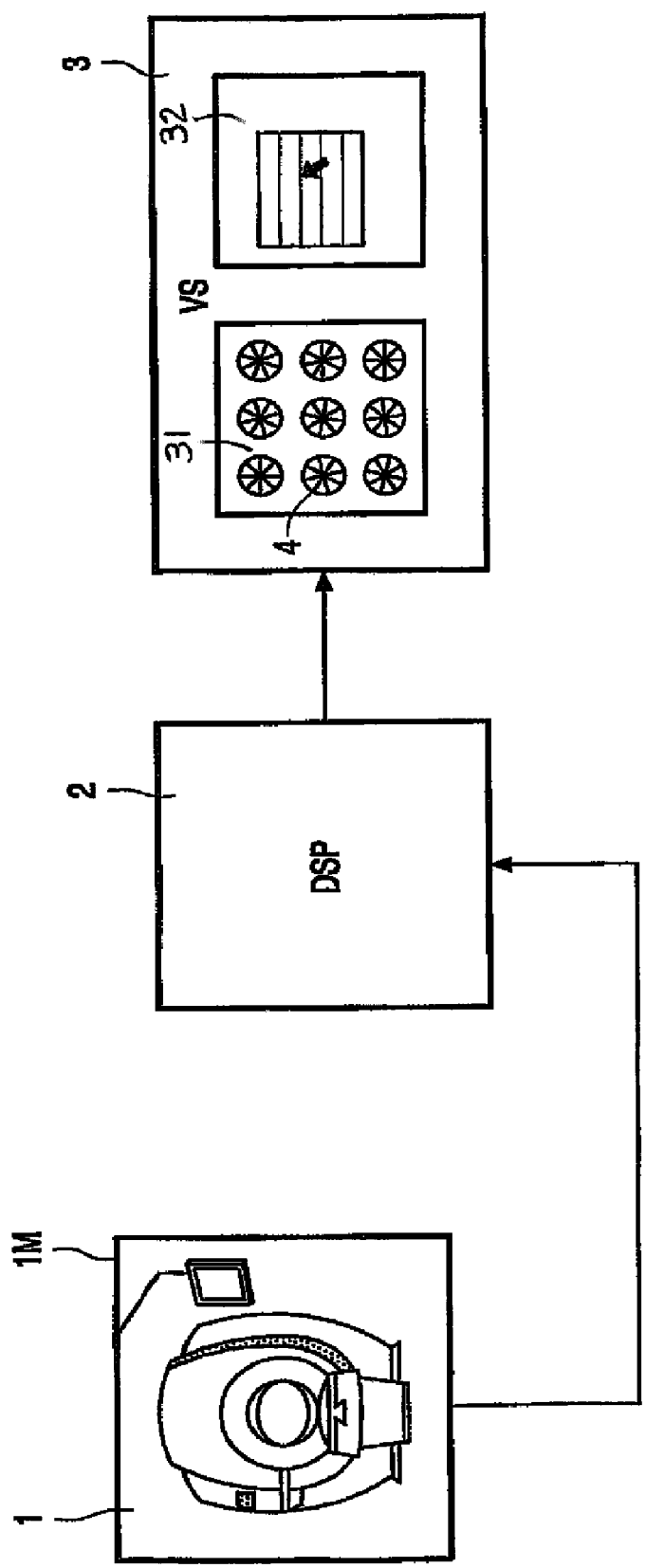

The invention relates to a method of analyzing a quantity having temporal and spatial variations, notably of analyzing perfusion of blood through the myocardium of a patient's heart.

Such a method of analyzing a quantity, notably of perfusion through the myocardium is known from the U.S. Pat. No. 5,803,914.

The known method displays information relating to the distribution of blood flow within the myocardium and information relating to the myocardium wall motion. This information on the myocardium is obtained in the known method from SPECT (single positron emission computed tomography) imaging data.

In particular, by the known method a display ring of arc sections of the myocardium is displayed with a color coding which depends on the perfusion ratio in each of the arc sections. The amount of the wall motion is represented by the thickness of the displayed arc. Inward and outward movement of the wall motion are indicated by extending the width of the arc section at issue towards or away from the center of the ring respectively. The known method displays a series of several, e.g. five, images of sequential frames. Hence, it is cumbersome to gain a good rendition of the perfusion process through the myocardium. Notably, the user of the known method needs to examine each individual section of the myocardium in several images. Further, the number of sequential frames that can be shown is limited severely by the capacity of the monitor on which the frames are shown.

An object of the invention is to provide a method of analyzing a varying quantity which furnishes an easy-reference rendition of the variations of the quantity. In particular, an object of the invention is to provide an easy-reference rendition of perfusion through the myocardium of a patient to be examined.

This object is achieved by a method according to the invention wherein
- a multidimensional output data array is formed
- the multidimensional output data array comprises array positions arranged along at least a first data-axis and a second data axis
- values of the quantity are entered in the multidimensional output data array, such that
    - values of the quantity at substantially the same instant are entered at respective positions in the multidimensional output data array at equal positions along the first data-axis and
    - values of the quantity at substantially the same spatial position are entered at respective positions in the multidimensional output data array at equal positions along the second data-axis.

The values of the quantity at issue are dependent on at least two variables. According to the invention the values of the quantity at issue are arranged in the multidimensional output data array as a function of these respective variables along the first and second data axis respectively. For example, the quantity at issue may be dependent on spatial position and time, a spatial position and temperature or the quantity at issue may depend on a radial and a tangential position relative to a predetermined center. In particular, the invention is advantageously employed in that the values of the quantity at issue are arranged in the multidimensional output data array as a function of time along the first data-axis and as a function of spatial position along the second data axis. The multidimensional output data array can be displayed as an output image. When a two-dimensional output data array is employed, the two-dimensional output data array itself can be displayed as an output image which shows the content of the multidimensional output data array. When three or more dimensions are employed, for example two-dimensional cross-sections through the multidimensional output data array, or a rendering or two-dimensional projection of the multidimensional output data array can be displayed as an output image. In the output image the pixel-values or voxel-values like grey-values, color-values or brightness values, correspond to the values in the multidimensional output data array. The positions of the pixels or voxels in the output image correspond to the positions in the multidimensional output data array.

The output image gives an easy-reference rendition of the time variation of the quantity at issue along the first data axis as the pixel variation in one direction in the output image. The output image also gives an easy-reference rendition of the spatial variation of the quantity at issue along the second data-axis as the pixel-variation in a second direction in the output image. Usually the first and second directions are orthogonal. Moreover, as the values of the quantity in neighboring spatial regions are displayed close to one another in the output image, differences between the temporal variations of the quantity in respective spatial regions can be very conveniently monitored. In particular, according to the invention the easy-reference rendition requires very few images to be examined. When a two-dimensional output data array is employed, even a single output image is sufficient to provide the easy-reference rendition of the variations of the quantity at issue. For example, when the invention is applied to perfusion through the myocardium, then differences in blood supply to respective sections of the myocardium served by individual coronary arteries are displayed in a single output image.

These and other aspects of the invention will be further elaborated with reference to the embodiments defined in the dependent claims.

Preferably, for respective spatial sections, values for the quantity are acquired and entered into the multidimensional output data array at their appropriate positions along the second data axis. The values of the quantity for the respective spatial sections represent the spatial variation of the quantity. For example for individual spatial sections a local average over the respective sections, a local minimum or local maximum value or the value at the center position of the spatial section at issue is used. It appears that in many applications such a representation on a per spatial section basis provides a fair representation of the spatial variations of the quantity at issue. Namely, the values of the quantity for individual sections give an accurate representation of the way the quantity varies spatially from section to section. The use of values for the quantity for respective spatial sections achieves a reduction of the amount of data to be processed. Notably, when the values of the quantity are derived from a series of images, the amount of data involved in the multidimensional output data array is far less than the amount of data involved in the images themselves, especially when high-resolution images of a high diagnostic quality are employed. The differences between the temporal variations of the quantity at individual spatial sections are easily viewed in the output image formed from the multidimensional output data array. Namely, the rendition of the values of the quantity along the first data axis forms time-traces of the quantity. Respective time-traces are formed for individual spatial sections and rendered at respective positions of the second data axis.

The amount of data is further reduced by using values of the quantity for respective time intervals. The value at respective successive time intervals provides a temporal sampling of the value of the for example continuously varying quantity.

Preferably, values of the quantity for adjacent spatial sections are entered at adjacent positions in the multidimensional output data array and correspondingly shown at adjacent positions in the rendition of the multidimensional output data array as an image. This allows spatially variations of the value of the quantity and of the temporal variation of the quantity to be clearly rendered visible in that these variations appear as relative sudden changes in the multidimensional output data array.

In another preferred implementation values of the quantity for spatially radially adjacent positions are entered at adjacent array positions in the multidimensional output data array. Consequently, in the rendition of the multidimensional output data array as an image radial variations of the quantity are clearly displayed. For example when applied to the examination of perfusion through the patient's myocardium, radial variations of the perfusion are important indications for disfunctioning parts in the coronary arterial system.

The values of the quantity at issue, notably perfusion through the patients myocardium are conveniently obtained from a series of diagnostic images. For example diffusion-weighted magnetic resonance images are used to obtain local values of perfusion of blood through tissue, such as the myocardium. From individual images, values of the quantity for several positions are obtained. From successive images, values of the quantity at successive instants are obtained, notably in that the successive images are acquired at successive instants in time.

In a further preferred implementation of the method of the invention individual positions in the multidimensional output data array are linked to the corresponding positions in the images from which the values of the quantity are derived. Notably, a link is provided between the spatial section and the temporal instants from which respective values of the quantity are derived. Thus, when an interesting feature is noticed in the rendition of the multidimensional output data array, the user may indicate that interesting feature. Then the method according to the invention automatically indicates the corresponding position in the corresponding image in the series. There are several ways to implement such a link. In a simple example the position of the indicated position on the displayed multidimensional output data array is calculated. From this calculated position in the multidimensional output data array the corresponding image in the series is derived as well as the corresponding spatial position in the image at issue, notably the position of the corresponding section in the image at issue. Then a marker is placed at the corresponding position in the image at issue. In another implementation a look-up table is provided with represents the correspondence between positions in the multidimensional output data array and positions (of the sections) in the images in the series. The indication of positions in the displayed multidimensional output data array can be done by way of a cursor in the form of an arrow or another symbol under control by a e.g. a mouse, joy-stick, touch screen.

Preferably, upon indication of a position in the rendition of the multidimensional output data array the image at issue from the series is automatically displayed and the position is marked in the image linked to the indicated position in the multidimensional output data array. For a notable feature in the multidimensional output data array the corresponding position in the image at issue is then easily provided. On the other hand, a position in one of the images can be indicated and automatically the corresponding position in the multidimensional output data array is marked. For a suspect feature in one of the images at issue, the corresponding position in the multidimensional output data array is easily provided and the variation of the quantity at the suspect feature is easily examined.

When applied to the examination of perfusion, the method provides an easy way to note interesting perfusion features from the rendition of the multidimensional output data array and the method also provides an easy reference to the corresponding position in the image at issue that also shows the local anatomic details in which the noted perfusion feature occurs. This implementation is in particular advantageous when employed for studying myocardial perfusion. Deviations from normal perfusion can be easily referenced to the relevant part of the anatomy of the myocardium. In particular, this implementation provides an advantageous tool for the cardiologist to detect local malfunctions in the coronary arterial system.

The invention also relates to a data processing system. A data processing system according to the invention is defined in claim 11. The data processing system is advantageously used to perform the method of analyzing the quantity such as perfusion through the patient's myocardium. For example the data processing system is coupled to or included in an magnetic resonance imaging system which acquires diffusion-weighted magnetic resonance signals and derives the values of the quantity at issue. A computer program according to the invention is defined in claim 12. The computer program according to the invention can be loaded into the working memory of a processor, such as a data processing system so as to enable the processor to perform the method according to the invention. The computer program according to the invention may be made available from a data carrier such as a CD-rom or may be downloaded from a data network such as the world-wide web.

These and other aspects of the invention will be elucidated with reference to the embodiments described hereinafter and with reference to the accompanying drawing wherein FIG. 1 shows a schematic representation of a cardiology image management system in which the method of the invention is employed.

Figure 2:
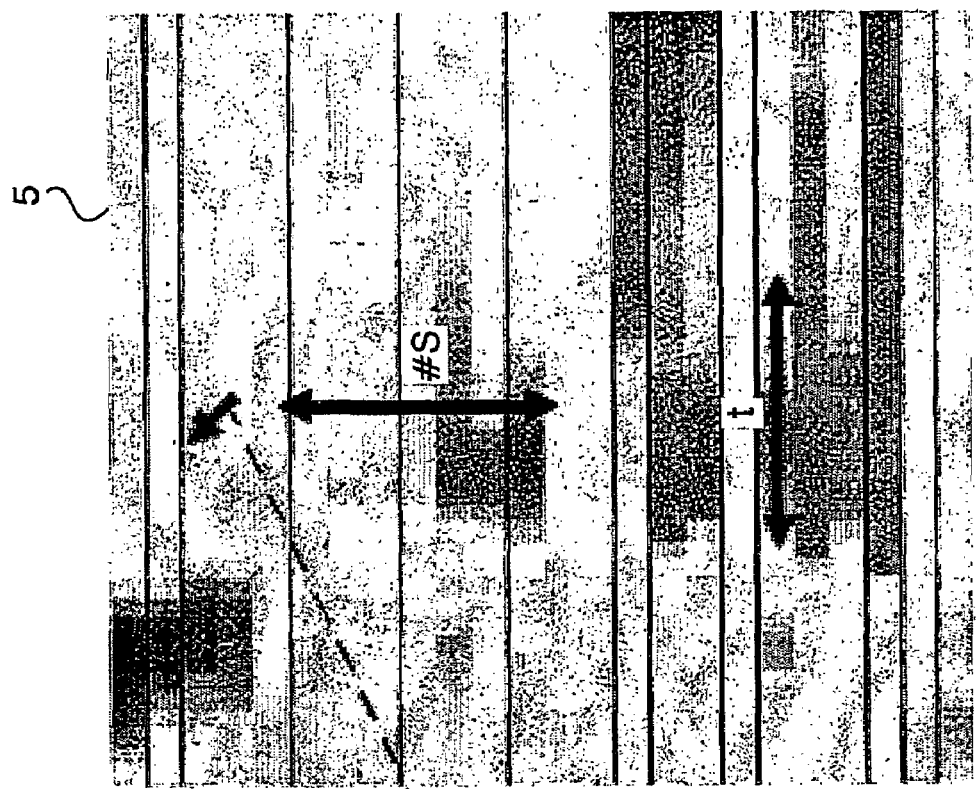
Figure 2:
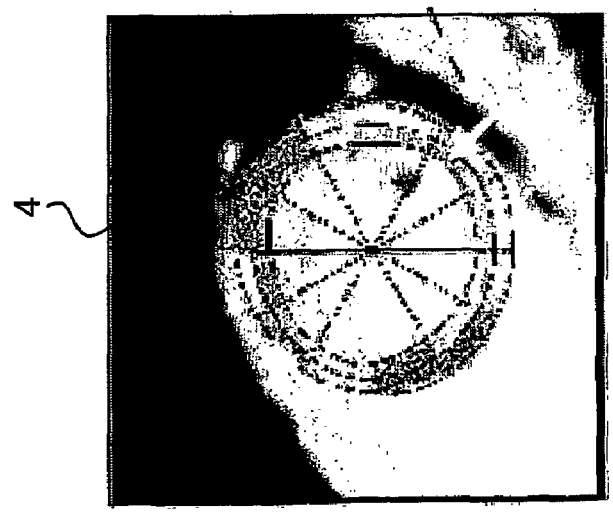

FIG. 2 shows a diagrammatic representation of an example of the relation of a series of images to the multidimensional output data array formed according to the invention.

FIG. 1 shows a schematic representation of a cardiology image management system in which the method of the invention is employed. The cardiology image management system includes an imaging modality 1 (IM) which supplies image data to the data processing system 2 (DSP). The data processing system derives the multidimensional output data array from the image data. The multidimensional output data array is then applied to a display system 3. Also the image data from the imaging modality 1 are supplied to the data processing system. The multidimensional output data array is displayed on the display system together with the image data. Optionally, image processing may be applied to these image data by the data processing unit to improve the rendition of the image data on the display system. In the example shown in FIG. 1, the imaging modality is a magnetic resonance imaging system which generates the image data in the form of perfusion images of for example the patient's myocardium. On the display system the series of myocardial perfusion images are shown with the multidimensional output data array. To this end the display system may comprise several display screens, or several display windows 31,32 may be opened on a display area FIG. 2 shows a diagrammatic representation of an example of the relation of a series of images from to the multidimensional output data array formed according to the invention.

In particular, FIG. 2 shows by way of example one of the myocardial perfusion images 4. The image of the myocardium is divided into several rings and individual rings are split into several sectors. The rings have the middle of the image of the left ventricle as their common center. The sectors extend mainly tangentially, that is transverse to the radial direction from the common center. The sectors are numbered essentially spirally outward, that is in an individual ring, the sectors are numbered for example increasing in the clockwise direction and the numbering also increases when going from an inner ring to a more outward ring. Although only a single myocardial perfusion image is shown in FIG. 2, this single image is one in a temporal series of myocardial perfusion images which show the temporal progress of the perfusion of blood through the patient's myocardium. FIG. 2 also shows the multidimensional output data array 5, corresponding to the series of myocardial perfusion images. In the example of FIG. 2, the first data axis is the time axis (t) and the second data axis represents the number of the sector (#S). In the multidimensional output data array, the data values of the series of myocardial perfusion images are plotted. In particular, for respective sectors in the individual myocardial perfusion images the average brightness value is computed in the data processing system. These average brightness values present the local amount of perfusion of blood through the myocardium. In the multidimensional output data array as displayed, along the time axis, time traces of the perfusion process for the respective sectors are produced. Along the vertical direction, i.e. the axis representing the sector number spatial differences of the perfusion in adjacent sectors are easily referenced.

The positions in the multidimensional output data array are linked to respective sectors in the respective image of the series. The user may indicate a specific position, e.g. where a striking change of brightness variations in the multidimensional output data array occurs. Such an indication may be done for example by a simple mouse-click at the position in the displayed multidimensional output data array. Upon indication by the user of a position in the displayed multidimensional output data array, the myocardial perfusion image linked to the indicated position is put on the display screen and the sector at issue is indicated for example by the white arrow shown in FIG. 2. The myocardial perfusion image linked to the indicated position may be displayed enlarged in stead of the complete series, or may be displayed in an additional window opened on the display screen. The myocardial perfusion image linked to the indicated position provides additional information on the patient's anatomy, notably the structure of the tissue in the sector at issue in the area where the interesting perfusion event shows up in the multidimensional output data array.

The invention claimed is:

1. A method of analyzing a quantity indicative of blood perfusion through a myocardium by analyzing a varying quantity which furnishes an easy reference rendition of the variations of the quantity, the quantity having temporal and spatial variations, including:
obtaining a multidimensional output data array, the multidimensional output data array comprising array positions arranged along at least a first data-axis and a second data-axis; and
receiving with a processor values corresponding to the quantity indicative of blood perfusion through tissue based on time series perfusion images generated from image data acquired by a tomographic imaging system;
wherein first values corresponding to the quantity at substantially a same instant in time are mapped by the processor to respective positions in the multidimensional output data array at equal positions along the first data-axis, and second values corresponding to the quantity at substantially a same spatial position are mapped by the processor to respective positions in the multidimensional output data array at equal positions along the second data-axis.

2. The method as claimed in claim 1, further including:
acquiring the first and second values of the quantity for respective temporal instants and for respective spatial sections; and
mapping the second values of the quantity for individual spatial sections to respective positions in the multidimensional output data array at equal positions along the second data-axis.

3. The method as claimed in claim 1, further including acquiring the first and second values of the quantity for respective time intervals and for respective spatial positions and mapping the first values of the quantity for individual time intervals to respective positions in the multidimensional output data away at equal positions along the first data-axis.

4. The method as claimed in claim 1, further including mapping the first values of the quantity for successive time intervals to adjacent positions in the multidimensional output data array; and mapping the second values of the quantity for adjacent spatial sections to adjacent positions in the multidimensional output data array.

5. The method as claimed in claim 4, further including mapping the second values of the quantity for radially contiguous spatial sections to contiguous positions in the multidimensional output data array.

6. The method as claimed in claim 1, wherein the first and second values of the quantity are derived from the time series perfusion images.

7. The method as claimed in claim 1, wherein the first values of the quantity at respective instants of time are derived from respective images in said time series perfusion images.

8. The method as claimed in claim 7, further including linking respective positions in the multidimensional output data away to respective spatial sections in respective images of the time series perfusion images.

9. The method as claimed in claim 8, further including:
displaying the multidimensional output data array;
indicating a position in the displayed multidimensional output data array; and
displaying the respective image of the time series perfusion images on the basis of the respective indicated position in the displayed multidimensional output data away and marking the respective spatial section in the image.

10. The method as claimed in claim 1, wherein the quantity pertains to perfusion of the myocardium.

11. A data processing system adapted to analyze a quantity indicative of blood perfusion through a myocardium by analyzing a varying quantity which furnishes an easy reference rendition of the variations of the quantity, the quantity having temporal and spatial variations, the system comprising:
a processor that obtains a multidimensional output data array, the multidimensional output data away comprising array positions arranged along at least a first data-axis and a second data-axis and that receives values corresponding to the quantity indicative of blood perfusion through tissue based on time series perfusion images generated from image data acquired by a tomographic imaging system;

wherein first values corresponding to the quantity at substantially a same instant in time are mapped by the processor to respective positions in the multidimensional output data away at equal positions along the first data-axis, and second values corresponding to the quantity at substantially a same spatial position are mapped by the processor to respective positions in the multidimensional output data array at equal positions along the second data-axis.

12. A computer-readable medium having stored therein computer executable instructions that when executed on a computer perform a method of analyzing a quantity indicative of blood perfusion through a myocardium by analyzing a varying quantity which furnishes an easy reference rendition of the variations of the quantity, the quantity having temporal and spatial variations, including causing the computer to:

obtain a multidimensional output data array, the multidimensional output data array comprising array positions arranged along at least a first data-axis and a second data-axis;

receive values corresponding to the quantity indicative of blood perfusion through tissue based on time series perfusion images generated from image data acquired by a tomographic imaging system;

wherein first values corresponding to the quantity at substantially a same instant in time are mapped to respective positions in the multidimensional output data array at equal positions along the first data-axis, and second values corresponding to the quantity at substantially a same spatial position are mapped to respective positions in the multidimensional output data array at equal positions along the second data-axis.

13. The method of claim 1, further comprising displaying the multidimensional output data array.

14. The method of claim 13, wherein the values of the quantity are derived from the image data, and further comprising displaying the image data while displaying the multidimensional output data array.

15. The method of claim 1, wherein the quantity is an average brightness value of the image data.

16. The method of claim 15, wherein the image data comprises perfusion data of a human myocardium.

17. The system of claim 11, further comprising a display device adapted to display the multidimensional output data array.

18. The system of claim 17, wherein the values of the quantity are derived from the image data, and wherein the display device is further adapted to display the image data while displaying the multidimensional output data array.

19. The system of claim 11, wherein the quantity is an average brightness value of the image data.

20. The system of claim 19, wherein the image data comprises perfusion data of a human myocardium.

* * * * *